United States Patent [19]

Koehler et al.

[11] Patent Number: 4,480,098

[45] Date of Patent: Oct. 30, 1984

[54] PREPARATION OF ALKALI METAL THIENO(FURO)PYRIDINES

[75] Inventors: Richard E. Koehler; John A. Webber, both of Indianapolis, Ind.

[73] Assignee: Eli Lilly and Company, Indianapolis, Ind.

[21] Appl. No.: 441,136

[22] Filed: Nov. 12, 1982

[51] Int. Cl.$^3$ ................. C07D 495/04; C07D 491/048
[52] U.S. Cl. .................................... 546/114; 546/115; 546/116
[58] Field of Search ...................... 546/114, 115, 116

[56] References Cited

FOREIGN PATENT DOCUMENTS 2105719  3/1983  United Kingdom .

OTHER PUBLICATIONS

Barker, *Adv. in Het. Chem.,* 21, 96 (1977).
Gronowitz et al., *Ark. Kemi.,* 32, 249 (1970).

*Primary Examiner*—Henry R. Jiles
*Assistant Examiner*—Bernard I. Dentz
*Attorney, Agent, or Firm*—Charles W. Ashbrook; Arthur R. Whale

[57] ABSTRACT

Thienopyridines and furopyridines react at the 2-position with non-nucleophilic alkali metal bases to give alkali metal thieno(furo)pyridine salts.

20 Claims, No Drawings

PREPARATION OF ALKALI METAL THIENO(FURO)PYRIDINES

BACKGROUND OF THE INVENTION

This invention concerns a process for making certain thienopyridine and furopyridine 2-anionic salts.

Thienopyridines and furopyridines bearing no substituents are well known. Substituted thieno (furo)-pyridines are less well known because of the difficulty of synthesis. Maffrand and Boigegrain recently have disclosed a synthesis of certain 2-substituted thieno[3,2-c]pyridines by thermal rearrangement of thienyl oxazolidines; Heterocycles Vol. 12, No. 11, 1479 (1979). Direct electrophilic substitution of unsubstituted thieno(furo)pyridines has not afforded 2-substituted thieno(furo)pyridines, presumably due to the relative unreactivity of the 2-position. Indeed, both thieno[3,2c] and thieno [2,3c]pyridines have been shown not to react at the 2-position with strong bases such as n-butyl lithium to form the 2-anion; see Advances in Heterocyclic Chemistry, 21, 96 1977. Dressler and Joullie reported that electrophilic attack occurred only at the 3-position in all of the thienopyridines that were studied; J. Heterocyclic Chemistry, 7, 1257 (1970).

An object of this invention is to provide a convenient process for preparing thieno(furo)pyridine 2-anionic salts from the corresponding 2-unsubstituted thieno(furo)pyridines by reacting a thieno(furo)pyridine with a non-nucleophilic alkali metal base.

SUMMARY OF THE INVENTION

This invention provides a process for preparing certain ionic salts of thieno(furo)[2,3-c] or [3,2-c] pyridines. More particularly, the invention is a process for preparing a compound of the formula

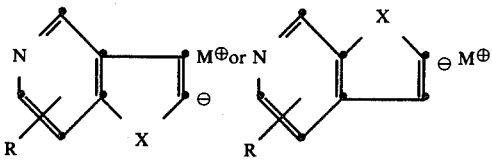

wherein:

R is hydrogen or $C_1$–$C_4$ alkyl;
X is O or S; and
$M^\oplus$ is an alkali metal cation such as sodium, lithium or potassium;
comprising reacting a compound of the formula

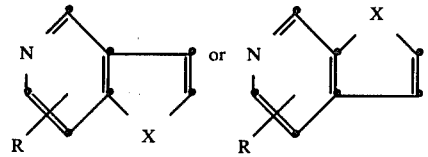

with a non-nucleophilic alkali metal base in an unreactive solvent at a temperature of about −100° to about −30° C.

A preferred embodiment employs a thienopyridine as substrate.

The most preferred embodiment employs lithium diisopropylamide as the non-nucleophilic alkali metal base to form compounds of the above formula wherein $M^+$ is $Li^+$.

DETAILED DESCRIPTION OF THE INVENTION

According to the process of this invention, a thieno(furo)pyridine that is unsubstituted at the 2-position is reacted with a non-nucleophilic alkali metal base. The thieno(furo)pyridine substrate that is employed can bear a lower alkyl substituent in the pyridine ring if desired. Typical thieno(furo)pyridines to be employed include 4-methylthieno[3,2-c]pyridine, 6-ethylfuro[3,2-c]pyridine, 7-n-butylthieno[3,2-c]-pyridine, 4-n-propyl-thieno[3,2-c]pyridine, 5-isobutylfuro[2,3-c]pyridine, and the like. All that is required is that the thieno [furo]-pyridine be unsubstituted at the 2-position.

The non-nucleophilic alkali metal base to be employed in the process includes any alkali metal base having a relative pKa value of about 25 to about 50 and that substantially fails to react with the C=N bond of the pyridine ring. Typical non-nucleophilic alkali metal bases that can be employed include the alkali metal di-lower alkyl amides such as lithium diisopropylamide, potassium diisopropylamide, sodium diisopropylamide, and lithium di-tert-butylamide; and the alkali metal silylazides such as lithium hexamethyl disilylazide and potassium hexamethyl disilylazide. A particularly preferred non-nucleophilic alkali metal base to be employed in the process is lithium diisopropylamide.

The base to be utilized generally is prepared in situ by routine procedures. For example, lithium diisopropylamide typically is prepared in situ by reaction of diisopropylamine with a strong alkyl lithium base, for example n-butyl lithium or methyl lithium. This in situ reaction is generally carried out in an unreactive solvent that is to be employed for the entire process. Suitable unreactive solvents include ethers such as diethyl ether, diisopropyl ether, methyl ethyl ether; cyclic ethers such as tetrahydrofuran and dioxane, as well as alkanes and cyclic alkanes such as n-hexane, n-pentane, cyclohexane, and the like. A preferred reaction solvent is tetrahydrofuran.

The in situ formation of the non-nucleophilic alkali metal base generally is carried out by reacting approximately equimolar quantities of an appropriate substrate such as diisopropylamine with a strong base such as n-butyl lithium, although an excess of either reactant can be employed if desired. This in situ reaction generally is carried out at a reduced temperature of about −30° to about −10° C., and routinely is substantially complete within about thirty to about ninety minutes.

Once the non-nucleophilic alkali metal base has been formed, the reaction temperature is generally lowered to about −100° to about −50° C., and then the thieno(furo)pyridine that is unsubstituted at the 2-position is added to the reaction mixture. A slight excess of the alkali metal base relative to the thieno(furo)pyridine, for example about a 0.1 to about 0.3 molar excess, generally is employed to ensure complete conversion of the thieno(furo)pyridine to the alkali metal thieno(furo)pyridine salt. Such alkali metal intermediate salts are formed, for example, from thieno[3,2-c]pyridine, thieno[2,3-c]pyridine, furo[3,2-c]pyridine, and furo[2,3-c]pyridine.

The alkali metal thieno(furo)pyridine salts are generally formed after about fifteen to about ninety minutes when the reaction is conducted at about −100° to about −50° C. The salts that are produced can be isolated by simply removing the reaction solvent, for example by evaporation under reduced pressure. Care should be taken to maintain the temperature of the thieno(furo)-pyridine 2-anionic salts below about −30° C. in order to minimize the risk of degradation. The salts also should be maintained in a relatively dry environment, since they readily are decomposed by reaction with water.

The thieno(furo)pyridine 2-anionic salts prepared by the new process are useful as intermediates in the synthesis of 2-substituted thieno(furo)pyridines. For example, reaction of the anionic salts with compounds that contain an electropositive group capable of reacting with a thieno(furo)pyridine 2-anion affords 2-substituted thieno(furo)pyridines of the formula

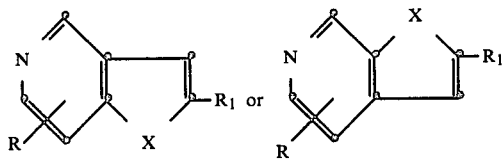

wherein R and X are as defined above and $R_1$ is, for instance, $C_1$–$C_4$ alkyl, halo, carboxy, amino, $C_1$–$C_4$ alkoxycarbonyl, —$SO_3H$, —CHO and the like As noted above, the thieno(furo)pyridine 2-anionic salts require storage at low temperatures and in the substantial absence of moisture in order to obviate risk of degradation. Because of this relative instability, it is sometimes desirable not to isolate the salt, but rather to employ it directly by reacting it in situ with a compound containing an electropositive group defined by $\delta + R_1$. For example, a preferred 2-substituted thieno(furo)pyridine to be prepared is a 2-carboxy thieno(furo)pyridine. Such compounds are prepared by simply adding carbon dioxide to the reaction solution containing the alkali metal thieno(furo)pyridine salt, followed by an aqueous acid workup.

Compounds containing $R_1$ that can be employed to provide a source of $\delta + R_1$ are well known in the art. For example, when a 2-substituted thieno(furo)pyridine wherein the 2-substituent is a $C_1$–$C_4$ alkyl group is desired, the process is carried out employing a $C_1$–$C_4$ alkyl halide such as methyl chloride or n-butyl iodide as the source of $\delta + R_1$.

Compounds to be employed when 2-($C_1$–$C_4$ alkoxycarbonyl) thieno(furo)pyridines are desired include $C_1$–$C_4$ alkyl haloformates such as methyl chloroformate, ethyl bromoformate, tert. butyl iodoformate, and the like.

Any compound that is capable of providing a source of halogen cations can be employed to produce 2-halothieno(furo)pyridines. Exemplary of such electrophiles are the trifluoromethyl halides such as trifluoromethyl bromide and trifluoromethyl iodide. Other compounds that can be employed to produce 2-halothieno(furo)-pyridines are the molecular halogens, for instance chlorine, bromine and iodine, and p-toluene sulfonyl halides such as p-toluenesulfonyl chloride.

Formamides generally are employed to produce 2-formylthieno(furo)pyridines. Orthoformates can also be employed. A preferred substrate for producing compounds of the above formula wherein $R_1$ is CHO is N,N-dimethylformamide.

Amination of thieno(furo)pyridine 2-anionic salts can be accomplished by employing nitrogen containing substrates such as α-azido styrene.

Typical substrates to be employed in the synthesis of 2-sulfonylthieno(furo)pyridines include sulfur trioxide or complexes of sulfur trioxide such as sulfur trioxide-dioxane and the like As pointed out above, the alkali metal thieno(furo)-pyridine salts generally are formed after about fifteen to about Ninety minutes of reaction with the non-nucleophilic alkali metal base at about −100° to about −50° C. The $R_1$ containing reagent is then simply added to the reaction mixture, generally in a portion-wise manner so that the temperature of the reaction is maintained below about −40° C. Following the addition of the reagent, the reaction temperature normally is maintained at about −70° to about −40° C. for about thirty to about sixty minutes, and then is allowed to rise to about −40° to about 0° C. over about a one to two hour period. The reaction can then be worked up and the product isolated by adding an acid to the mixture to quench any remaining base. Typical acids commonly employed for this purpose include glacial acetic acid, concentrated hydrochloric acid, formic acid, concentrated sulfuric acid, and the like. Once any remaining base has been destroyed, the reaction solvent can be removed, for instance by evaporation under reduced pressure, and the product, a 2-substituted thieno(furo)-pyridine, can be further purified if desired by routine methods such as acid and base extractions, column chromatography, crystallization, and related techniques.

The 2-substituted thienopyridines and 2-substituted furopyridines thus prepared have been found particularly valuable as intermediates in the synthesis of certain cephalosporin antibiotics. For example, a 3-iodomethylcephalosporin has been found to readily react with a 2-substituted thieno(furo)pyridine to give a 3-[2-substituted thieno(furo)pyridinium]cephalosporin compound that is, or is readily converted to, a potent antibacterial agent.

The following examples are provided in an effort to illustrate specific embodiments of the present process.

EXAMPLE 1

2-Methylthieno[3,2-c]pyridine

To a cold (−25° C.) stirred solution of 3.63 g (36 mM) of freshly distilled diisopropylamine in 50 ml of tetrahydrofuran (THF) were added dropwise over ten minutes 22 ml (35 mM) of a 1.6 molar solution of n-butyl lithium in hexane. The reaction mixture was stirred under a nitrogen blanket at −25° C. for fifteen minutes following the addition, and then the temperature was reduced to −70° C. While maintaining the reaction temperature at about −70° to −65° C., a solution of 4.05 g (30 mM) of thieno[3,2-c]pyridine in 50 ml of THF was added to the reaction mixture dropwise over fifteen minutes to form the desired salt, namely lithium thieno[3,2-c]pyridine. This product was not isolated, but rather was reacted in situ. While the reaction mixture was stirred at about −65° C., a solution of 5.0 g (35 mM) of methyl iodide in 25 ml of THF was added dropwise. Following complete addition of the methyl iodide solution, the reaction mixture was stirred and warmed gradually to −40° C. over a two hour period. The reaction mixture was next diluted by the addition of 5.0 ml of glacial acetic acid and warmed to 0° C. The reaction solvent was then removed by evaporation under reduced pressure to provide the product as a crude oil. The oil was dissolved in dichloromethane and water, and the pH was adjusted to 1.0 by addition of 5% aqueous hydrochloric acid. The aqueous acid layer was washed several times with fresh dichloromethane, and then made basic to pH 11.5 with conc. sodium hydroxide. The aqueous alkaline mixture was extracted several times with fresh dichloromethane, and the extracts were combined, washed with water, dried, and the solvent was removed by evaporation to give 2.81 g of 2-methylthieno[3,2-c]pyridine. mp 47°-48° C. The product thus obtained was further purified by chromatography over silica gel, eluting with dichloromethane.

Analysis calc. for $C_8H_7NS$
Theory: C, 64.40; H, 4.73; N, 9.39.
Found: C, 64.19; H, 4.85; N, 9.25.
nmr ($CDCl_3$) $\delta 2.50$ (s, 3H, $CH_3$); $\delta 6.85$ (m, 1H, $C_3$); $\delta 8.30$ (d, 1H, $C_7$); $\delta 8.85$ (5, 1H, $C_4$);
UV $\lambda_{max}225$.

EXAMPLE 2

2-Ethoxycarbonylthieno[3,2-c]pyridine

Following the general procedure set forth in Example 1, 8.1 g (60 mM) of thieno[3,2-c]pyridine in 50 ml of THF were added to a stirred cold ($-25°$ C.) solution of lithium diisopropylamide (prepared in situ from 7.26 g of diisopropylamine and 44 ml of n-butyl lithium) to form lithium thieno[3,2-C]pyridine. The reaction mixture was then cooled to $-72°$ C. and stirred while a solution of 5 g of ethyl chloroformate in 20 ml of THF was added dropwise. The reaction mixture was then stirred at $-65°$ C. for forty-five minutes, and then was warmed to $-50°$ C. and diluted with 5 ml of glacial acetic acid The reaction mixture was warmed to $-5°$ C. and then the reaction solvent was removed by evaporation under reduced pressure. Isolation and purification according to the method described in Example 1 afforded 22 mg of 2-ethoxycarbonylthieno[3,2-c]pyridine.

EXAMPLE 3

2-Carboxythieno[3, 2c]pyridine

Freshly distilled diisopropylamine (18.15 g, 180 mMole) was dissolved in 200 ml of sieve-dried tetrahydrofuran. The solution was cooled to $-20°$ C., and stirred under a nitrogen blanket while n-butyl lithium (176 mM) was added, with care being taken to ensure that the temperature did not rise above $-20°$ C. The temperature of the reaction mixture was then dropped to $-70°$ C. using dry ice/acetone. A solution of 20.25 g of thieno[3,2-c]pyridine (150 mM) in tetrahydrofuran was added dropwise taking care to ensure that the temperature did not rise above $-65°$ C. The addition was complete after 20 minutes during which period stirring was continued. The product, lithium thieno[3,2-c]-pyridine, was not isolated. Carbon dioxide gas was bubbled into the reaction mixture in such a way that the temperature remained below $-60°$ C. for 30 minutes, $-40°$ C. for 1 hour and, finally, under $-15°$ C. for 30 minutes. The reaction solvent was removed by evaporation under reduced pressure and the residue was dissolved in water. The aqueous diisopropylammonium salt of 2-carboxythieno[3,2-c]pyridine thus formed was washed three times with methylene chloride, and then 120 ml of 5N sodium hydroxide were added. Cooling in ice water with stirring resulted in the precipitation of the sodium salt of 2-carboxythieno[3,2-c]pyridine (24.8 g, after filtration under vacuum and drying).

This sodium salt was then dissolved in 10% aqueous methanol and the solution acidified to pH 6.0 with concentrated hydrochloric acid. After filtration and drying under vacuum there was obtained 19 G of 2-carboxythieno[3,2-c]pyridine.

NMR ($DMSOd_6$): signals at 8.1 (d, 1 proton), 8.2 (s, 1 proton), 8.5 (d, 1 proton), 9.1 (s, 1 (proton)

EXAMPLE 4

2-Iodothieno[3,2c]pyridine

A solution of 3.63 g (36 mM) of freshly distilled diisopropylamine in 50 ml of THF was cooled to $-20°$ C. and stirred while a solution of 22 ml of 1.6M n-butyl lithium in hexane was added dropwise. Following the addition, the reaction mixture was cooled to $-70°$ C. and stirred while a solution of 4.05 g of thieno[3,2-c]pyridine in 30 ml of THF was added dropwise over fifteen minutes to give lithium thieno[3,2-c]-pyridine. While maintaining the reaction temperature at $-65°$ to $-70°$ C., a solution of 8 g of trifluoromethyl iodide in 40 ml of THF was added dropwise. Following the addition, the reaction mixture was stirred at $-65°$ to $-70°$ C. for one hour, and then was allowed to warm to $-5°$ C. over forty-five minutes.

The reaction mixture was next diluted with 5 ml of glacial acetic acid, and then the reaction solvents were removed by evaporation under reduced pressure to give an oil. The oil was dissolved in 200 ml of dichloromethane and extracted three times with 75 ml of water containing 25 ml of 5% hydrochloric acid. The aqueous extracts were combined, made basic to pH 10 by the addition of conc. sodium hydroxide, and then extracted several times with fresh dichloromethane. The organic extracts were combined, washed with water, dried, and concentrated to dryness to give 4.6 g of crude product. The product was crystallized from ethyl acetate and hexane to afford 2.1 g of 2-iodothieno[3,2-c]pyridine.

Analysis calc. for $c_7H_4NSI$
Theory: C, 32.20; H, 1.54; N, 5.36.
Found: C, 32.30; H, 1.73; N, 5.35.

EXAMPLE 5

2-Methylfuro[3,2-c]pyridine

To a stirred cold ($-15$ to $-20°$ C.) solution of 2.42 g of diisopropylamine in 30 ml of THF were added dropwise 15.7 ml of a 1.6 molar solution of n-butyl lithium in hexane. The reaction mixture was stirred under a nitrogen blanket for thirty minutes and then cooled to $-70°$ C. To the cold mixture were added 2.38 g of furo[3,2-c]pyridine in 20 ml of THF. Stirring was continued for twenty minutes at $-65°$ C. to give lithium furo[3,2-c]pyridine, which began precipitating out of solution. A solution of 3.4 g of methyl iodide in 20 ml of THF was added to the reaction mixture dropwise over fifteen minutes, and then the mixture was stirred at $-70°$ C. for thirty minutes and then allowed to warm to $-10°$ C. over forty-five minutes. The reaction mixture was then diluted with 5 ml of glacial acetic acid and the reaction solvent was removed by evaporation under reduced pressure. The residual product was dissolved in 50 ml of dilute hydrochloric acid, washed with dichloromethane, and then the aqueous acid solution was made basic to pH 10 with sodium hydroxide. The product was extracted into fresh dichloromethane, which was then dried and concentrated to dryness to give 2.3 g of 2-methylfuro[3,2-c]pyridine. nmr ($CDCl_3$): $\delta 2.47$ (s, 3H, $CH_3$); $\delta 6.40$ (m, 1H, $C_3$); $\delta 7.35$ (d, 1H, $C_6$); $\delta 8.37$ (d, 1H, $C_7$); $\delta 8.75$ (s, 1H, $C_4$).

EXAMPLE 6

2-Aminothieno[3,2-c]pyridine

To a cold (−70° C.) stirred solution of lithium diisopropylamide in THF, prepared in situ by reaction of 3.63 g of freshly distilled diisopropylamine and 22 ml of 1.6M n-butyl lithium in 50 ml of hexane, were added dropwise over twenty minutes 4.05 g (30 mMoles) of thieno[3,2-c]pyridine in 20 ml of THF. The reaction mixture was stirred for twenty minutes following the addition, and then was diluted by the dropwise addition of 5.22 g (36 mMoles) of α-azido styrene in 20 ml of THF. The reaction mixture was stirred for two hours while maintaining the temperature at −70° to −50° C.; and then for an additional hour while allowing the temperature to warm to −15° C. The reaction was then quenched by the addition of 50 ml of 5% aqueous hydrochloric acid. Removal of the reaction solvent by evaporation under reduced pressure afforded 3.0 g of crude product. Purification by chromatography over silica gel, eluting with ethyl acetate, afforded 1.2 g of 2-aminothieno[3,2-c]pyridine. Mass Spec. M+theory: 150, found: 150.

EXAMPLE 7

2-Formylthieno[3,2-c]pyridine

A solution of 1.6 g (15.8 mMoles) of diisopropylamine in 50 ml of dry THF was stirred under a nitrogen blanket and cooled to −25° C. The reaction solution was then diluted by the addition of 9.6 ml of a 1.6 Molar hexane solution of n-butyl lithium. The reaction mixture was stirred for twenty minutes at −25° C., and then was cooled to −70° C. and diluted by the dropwise addition of a solution of 1.7 g (13 mMoles) of thieno[3,2-c]pyridine in 50 ml of THF (temperature was maintained at −70° to −65° C. throughout the addition). Following complete addition of the thienopyridine, the reaction mixture was stirred at −70° C. for twenty minutes. A solution of 2.0 ml of N,N-dimethylformamide in 25 ml of THF was next added to the reaction mixture, and stirring was then continued at −70° C. for twenty minutes, and for an additional thirty minutes at −40° C. The reaction was quenched by the addition of 3 ml of glacial acetic acid, and then the mixture was warmed to 0° C. The reaction solvent was removed by evaporation under reduced pressure to provide the product as a crude oil. The oil was dissolved in water containing 1N hydrochloric acid to pH 1.0. The aqueous acid solution was extracted with dichloromethane, and then made alkaline to pH 11.5 with 1N sodium hydroxide. The alkaline solution was extracted several times with fresh dichloromethane, and the extracts were combined, dried, and the solvent was removed by evaporation under reduced pressure. Crystallization of the product thus formed from 500 ml of hot hexane afforded 800 mg of 2-formylthieno[3,2-c]pyridine.

Analysis calc. for $C_8H_5NOS$
Theory: C, 58.52; H, 3.68; N, 8.53.
Found: C, 58.67; H, 3.40; N, 8.43.

EXAMPLE 8

2-Bromothieno[3,2-c]pyridine

Lithium thieno[3,2-c]pyridine was prepared by first reacting 3.63 g (36 mMoles) of freshly distilled diisopropylamine in 50 ml of THF with 22 ml (35 mMoles) of a 1.6 M hexane solution of n-butyl lithium at −15° C. to give lithium diisopropylamide. The alkali metal non-nucleophilic base thus formed was reacted with 4.05 g (30 mMoles) of thieno[3,2-c]pyridine in 50 ml of THF at −70° C. The reaction mixture became dark red in color, indicating the presence of lithium thieno[3,2-c]-pyridine. The salt next was reacted in situ with 5.3 g of bromine (diluted with nitrogen), initially at −70° C. and then gradually to 0° C. The reaction solvent was removed by evaporation under reduced pressure to give an oil. The oil was dissolved in 50 ml of 5% aqueous hydrochloric acid. The aqueous acid mixture was washed with dichloromethane and then made alkaline with 50% aqueous sodium hydroxide. The alkaline solution was extracted several times with dichloromethane, and the organic extracts were combined, washed with water, dried, and the solvent was removed by evaporation to afford 3.4 g of product containing 2-bromothieno[3,2-c]pyridine. NMR (DMSO$_{d6}$) δ9.0 (1H,d); δ8.58 (1H,d); δ8.18 (1H,dd); δ7.03 (1H,d).

EXAMPLE 9 syn-7-[2-(2-aminothiazol-4-yl)-2-methoxyiminoacetamido]-3-(2-carboxythieno[3,2-c]pyridinium-5ylmethyl)-3-cephem-4-carboxylate To a stirred suspension of 1.82 g (4 mMoles) of syn-7-[2-(2-aminothiazol-4-yl)-2-methoxyiminoacetamido]-3-acetoxymethyl-3-cephem-4-carboxylate in 20 ml of acetonitrile were added 2.49 ml (14 mMoles) of N-methyl-N-trimethylsilyltrifluoroacetamide. The suspension was stirred at room temperature, and all solid material had dissolved after about thirty minutes. To the stirred reaction mixture were added 0.74 ml (5.2 mMoles) of trimethylsilyliodide and stirring was continued for twenty minutes. The reaction solvent was then removed by evaporation under reduced pressure to give the silylated 3-iodomethyl cephalosporin derivative. The 3-iodomethyl cephalosporin was dissolved in 35 ml of acetonitrile containing 0.89 ml of tetrahydrofuran and stirred while a solution of 859 mg (4.8 mMoles) of 2-carboxythieno[3,2-c]pyridine (prepared as described in Example 3) in acetonitrile was added in one portion. The reaction mixture was stirred for three and one-half hours at room temperature and then was diluted with 1 ml of water. Evaporation of the reaction solvents and purification of the product by high performance liquid chromatography gave 2.51 g of syn-7-[2-(2-aminothiazol-4-yl)-2-methoxyiminoacetamido]-3-(2-carboxythieno[3,2-c]pyridinium-5-ylmethyl)-3-cephem-4-carboxylate.

NMR (DMSO$_{d6}$); δ9.7 (S, 1H); δ9.5 (d, 1H);
δ9.0 (d, 1H); δ8.7 (d, 1H); δ8.1 (s, 1H);
δ7.1 (S, 2H); δ5.7 (q, 1H); δ5.3 (d, 2H);
δ5.1 (d, 1H); δ3.8 (S, 3H); δ3.4 (q, 2H). UV λ max 245 nm
ε=max 46,000

We Claim:

1. A process for preparing a compound of the formula

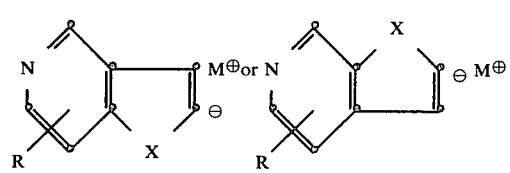

wherein:

R is hydrogen or $C_1$-$C_4$ alkyl;

X is O or S; and $M^{\oplus}$ is an alkali metal cation; comprising reacting a compound of the formula

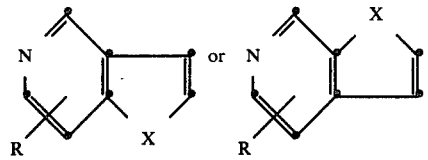

with a non-nucleophilic alkali metal base in an unreactive solvent at a temperture of about $-100°$ to about $-30°$ C.

2. The process according to claim 1 employing a thienopyridine substrate of the formula

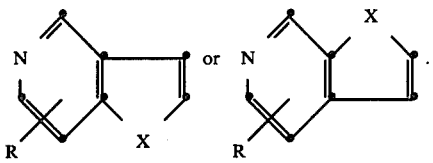

3. The process according to claim 2 employing thieno[3,2-c]pyridine as substrate.

4. The process of claim 1 wherein the nonnucleophilic alkali metal base is lithium diisopropylamide.

5. The process according to claim 4 comprising reacting thieno[3,2-c]pyridine with lithium diisopropylamide.

6. The process according to claim 1 employing a cyclic ether as the unreactive solvent.

7. The process according to claim 6 wherein the unreactive solvent is tetrahydrofuran.

8. The process according to claim 1 wherein X is O.

9. The process according to claim 1 wherein the product is reacted in situ with a compound containing an electropositive group capable of reacting with the thieno(furo)pyridine 2-anion to form a 2-substituted thieno(furo)pyridine of the formula

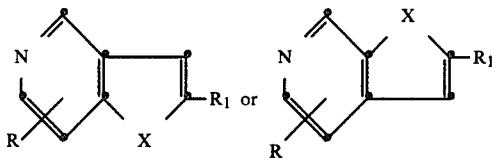

wherein:
R is hydrogen or $C_1$-$C_4$ alkyl;
X is O or S; and
$R^1$ is $C_1$-$C_4$ alkyl, halo, carboxy, amino, $C_1$-$C_4$ alkoxycarbonyl, $-SO_3H$ or $-CHO$.

10. The process according to claim 9 wherein the alkali metal thieno(furo)pyridine salt is reacted with a $C_1$-$C_4$ alkyl halide.

11. The process according to claim 9 wherein the alkali metal thieno(furo)pyridine salt is reacted with chlorine, bromine or iodine.

12. The process according to claim 9 wherein the alkali metal thieno(furo)pyridine salt is reacted with carbon dioxide followed by an aqueous acid workup.

13. The process according to claim 9 wherein the alkali metal thieno(furo)pyridine salt is reacted with a $C_1$-$C_4$ alkyl halo formate.

14. The process according to claim 9 wherein the alkali metal thieno(furo)pyridine salt is reacted with a formamide.

15. The process according to claim 9 wherein the alkali metal thieno(furo)pyridine salt is reacted with α-azido styrene.

16. The process according to claim 9 wherein the alkali metal thieno(furo)pyridine salt is reacted with sulfur trioxide or a complex containing sulfur trioxide.

17. The process according to claim 16 employing sulfur trioxide-dioxane complex.

18. A compound of the formula

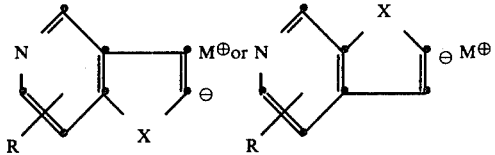

wherein:
R is hydrogen or $C_1$-$C_4$ alkyl;
X is O or S; and
$M^{\oplus}$ is an alkali metal cation.

19. The compound of claim 18 wherein R is hydrogen and $M^+$ is $Li^+$.

20. The compound of claim 19 wherein X is S.

* * * * *